United States Patent [19]
Park et al.

[11] Patent Number: 5,879,911
[45] Date of Patent: Mar. 9, 1999

[54] CELL SURFACE PROTEIN EXPRESSED ON HUMAN CORTICAL THYMOCYTE AND THEIR USE

[75] Inventors: Seong Hoe Park, Kangnam; Young Mee Bae, Seoul, both of Rep. of Korea

[73] Assignee: Seong Hoe Park, Kangnam-ku, Rep. of Korea

[21] Appl. No.: 782,682

[22] Filed: Jan. 15, 1997

Related U.S. Application Data

[62] Division of Ser. No. 247,985, May 23, 1994, Pat. No. 5,641,860.

[30] Foreign Application Priority Data

May 21, 1993 [KR] Rep. of Korea .................. 93-8796
May 20, 1994 [KR] Rep. of Korea ................ 94-11083

[51] Int. Cl.⁶ .............. A61K 39/395; A61K 39/44; C07K 16/28; G01N 33/53
[52] U.S. Cl. .............. 435/70.21; 435/326; 435/330; 530/387.1; 530/387.7; 530/388.1; 530/388.22; 530/391.1; 530/391.7; 530/350; 424/130.1; 424/133.1; 424/134.1; 424/141.1; 424/142.1; 424/145.1; 424/152.1; 424/155.1

[58] Field of Search ............... 530/387.1, 387.7, 530/388.1, 388.15, 388.22, 391.1, 391.7, 350; 424/130.1, 133.1, 134.1, 141.1, 142.1, 145.1, 152.1, 155.1

[56] References Cited

PUBLICATIONS

A. Lehuen et al., "Identification of a Surface Protein, (p100) Associated With Two . . . ," European Journal of Immunology, 22(9) : 2373–2380 (1992).

V. Santana et al., "Identification of a High Molecular Weight Protein on the Surface . . . ," European Journal of Immunology, 6(3) : 217–22 (1976).

Park et al., "JL1, A Novel Differentiation Antigen of Human Cortical Thymocyte," J. Exp. Med., 178:1447–1451 (1993).

*Primary Examiner*—Lila Feisee
*Assistant Examiner*—John Lucas
*Attorney, Agent, or Firm*—Finnegan, Henderson, Farabow, Garrett & Dunner, L.L.P.

[57] ABSTRACT

A novel protein which is glycoprotein with 120,000 molecular weight and is expressed on T lymphoblastic lymphoma and leukemia cells, is useful in the diagnosis of T lymphoblastic lymphoma and leukemia.

20 Claims, 4 Drawing Sheets

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear     ( i i ) MOLECULE TYPE: peptide     ( x i ) SEQUENCE DESCRIPTION: SEQ ID NO:1:

```
Val   Leu   Pro   Ser   Val   Phe   Cys   Ala   Ile   Thr
1                       5                             10
```

CELL SURFACE PROTEIN EXPRESSED ON HUMAN CORTICAL THYMOCYTE AND THEIR USE

This is a division of application Ser. No. 08/247,985 filed May 23, 1994 Now U.S. Pat. No. 5,641,860.

BACKGROUND OF THE INVENTION

1. Field of the Invention

The present invention relates to a cell surface protein expressed on human cortical thymocytes and its use. More particularly, the present invention relates to a novel protein (called "JL1" hereinafter) having molecular weight of about—120,000 dalton expressed exclusively on cortical thymocytes and on malignant cells of T lymphoblastic leukemia, T lymphoblastic lymphoma originated from cortical thymocytes and about 50% of all kinds of leukemia, which are identified by immunohistochemical and flow cytometric analysis, and to its diagnostic and clinical application on leukemia and T lymphoblastic lymphoma.

2. Description of Related Art

Human body shows the specific responses to foreign substances exposed after birth, and T- and B-lymphocytes and antigen presenting cells are involved in immune responses to protect human body. Lymphocytes are the major components of lymphoid organ cells and have an important role in the specific immune response during circulation through blood and lymph. The major role of B—lymphocytes is to produce antibodies against foreign substances. T lymphocytes are classified into two types, one of which has the function to help the specific immune response and the other has the function of killing cells infected by pathogens. And the role of antigen presenting cells is to engulf infecting antigens non-specifically, and to process them by cleaving into small peptides and provide their information to T lymphocytes.

Intrathymic T cell development entails complex series of proliferation, differentiation, and selection stages. T cells are originated from hematopoietic stem cells produced in embryonic liver and postnatal bone marrow. They move into thymus, differentiate, become mature, and after this, move out through blood vessel and become mature T cells. After rearrangement of T cell receptor germline gene in the thymus, thymocytes express T cell receptor complexes on their cell surfaces. The gene rearrangement process requires enzymatic system including RAG-1, RAG-2. As a result, extreme T cell receptor diversity can be produced in the course of this complicated process. However, all the T cell receptors produced cannot carry out their appropriate functions in periphery. The cells which cannot recognize the antigens provided by major histocompatibility complex (MHC) class I and class II, and cells which show strong response to self antigen are removed. These processes are called positive and negative selection, respectively. T cell receptors can accomplish their appropriate function when they recognize foreign antigen bound to their own MHC molecule on the cell surface. This educational process takes place in the thymus.

T cells express not only T cell receptors but also various cell surface proteins. These proteins are also important in T cell function. Most of these T cell surface proteins are expressed in a broad range of T cell subsets. However, some of them are expressed only at a specific stage and these proteins can be used as T cell surface markers for the determination of T cell maturation stage. Generally, the classification system by Renherz et al, using T cell surface molecules as markers, has been used for determing the differentiation stages of thymocytes. According to this classification, thymocytes are classified into (a) early thymocyte, $CD4^-/CD8^-$ double negative, (b) common thymocyte, $CD4^+/CD8^+$ double positive, and (c) mature thymocyte, $CD4^+$ or $CD8^+$ single positive. Early thymocytes express CD7, CD38 and CD71 proteins. They are the cells which recently arrive at the thymus from bone marrow and actively divide. The rearrangement of T cell receptor gene -$TCR\beta$- occurs at this stage. Common thymocytes occupy the largest portion of the thymus and begin to express CD1, CD2, CD3, CD4, CD5, CD8 and the like on cell surfaces, and $TCR\alpha$ genes are rearranged. Thereafter, mature thymocytes express T cell receptors on the cell surface. Only some of them can survive and move to the next stage, and most of them die (Nikolis-Zugic, 1991, *Immunol. Today, 12, 65–70*). The cell surface molecules in T cells and thymocytes can be used to determine the stage of differentiation and the classification of subsets. In addition, they can be used for the diagnosis and treatment of tumors originated from T cells. These cell surface proteins have an important role in function and development of T cell.

A thymocyte should die unless its T cell receptor is appropriate. And the death is not simply a passive death but an active death requiring certain proteins or the synthesis of certain metabolic products (Rothenberg, 1990, *Immunol. Today, 11, 116–119*). This cell death may require the specific stimulating signals from the outside. And the cell surface proteins may be involved in the signal pathway. However, identification of cell surface molecules involved has not been possible until now. If common thymocytes express the specific proteins to transmit the signals for the selection of T cell receptor and programmed cell death, these proteins would be the intrinsic proteins at that stage. Even though a few cortical thymocyte antigens such as CD1a, b and c have been known to be expressed on thymic cortex, they are also expressed on various types of cells such as dendritic cells, brain astrocytes and B lymphocytes.

SUMMARY OF THE INVENTION

An object of the present invention is to provide a novel protein which is expressed on cortical thymocytes which can be used to classify the developmental stage of cell.

Another object of the present invention is to provide a protein whose expression is restricted on thymocytes and tumor cells originated from hematopoietic system.

A third object of the present invention is to provide material to determine the developmental stage of thymocytes and diagnose the tumors originated from hematopoietic system.

A fourth object of the present invention is to provide therapeutic material which can kill tumor cells originated from hematopoietic system.

In addition, the present invention is to provide a method for treatment by use of the therapeutic material of the present invention.

The present invention provides a cell surface protein expressed on human cortical thymocytes, "JL-1". The cell surface protein above is a single chain glycoprotein with a approximately 120,000 dalton of molecular weight.

The protein of the present invention is expressed on human cortical thymocytes, and it is also expressed on cells of T lymphoblastic leukemia and lymphoma originated from human cortex thymocytes, and cells of about 50% of various types of leukemia.

Also, the present invention provides material recognizing the protein, JL-1. The material is selected from the group consisting of antibodies and ligands, and the antibody is preferably selected from the group consisting of monoclonal antibody and polyclonal antibody, and more preferably it is originated from human or animal. The antibody mentioned above comprise parts of antibody including antigen recognition region ($V_H$ and $V_L$), so has the capacity to recognize antigen specifically. And it also includes antibody fragment, such as F(ab')2, Fab and Fv. Preferably the antibody fragment (Fv) comprises a single chain polypeptide fragment of antigen, so called single chain Fv, which is prepared by inserting a linking peptide between two polypeptides, $V_H$ and $V_L$ to increase heat stability. The material above may comprise labelling material which is selected from the group consisting of radioisotope, fluorescent material and staining material.

The present invention also provides a method for producing the material above, and it provides a cell producing the material above and a method for producing the cell.

Further, the present invention provides a method for the diagnosis of T leukemia and T lymDhoblastic lymphoma using the material above.

In addition, the present invention provides a method for the treatment of leukemia and T lymphoblastic lymphoma using the material above, which is selected from the group consisting of antibody, antibody. fragment, single chain polypeptide antibody fragment and ligand. The antibody or the antibody fragment is preferably selected from the group consisting of monoclonal antibody and polyclonal antibody, and more preferably it is originated from human or animal. Preferably the antigen recognition material includes toxic protein which is selected from the group consisting of radioisotopes, toxic chemicals, toxic proteins and anti-tumor agents.

The present invention provides a method for treatment of leukemia and T lymphoblastic lymphoma originated from hematopoietic system by gene therapy using JL-1 protein as target material, and JL-1 recognition material as target pursuing material (guiding material).

In addition, the present invention provides a novel protein which is identified by a method comprising the steps of (a) producing antibody by administering human thymocytes into mouse and purifying the resulting antibodies; (b) collecting antibody which exclusively reacts to cortical thymocytes by immunohistochemical staining of thymus with said purified antibody of step(a); (c) collecting antibody which reacts only to the thymus by immunohistochemical staining of normal human tissues with said collected antibody of step(b); and (d) collecting protein which reacts to leukemia cell and T lymphoblastic lymphoma by immunohistochemical staining with said collected antibody of step (c).

DETAILED DESCRIPTION OF THE EMBODIMENTS

The following specific examples of biologically active polypeptides are illustrative of the present invention, but are not to be considered limiting thereof in any way.

EXAMPLE 1

In order to discover a specific cell surface protein on common thymocyte, human thymocytes were administered into Balb/c mice to produce antibodies to human thymocytes by the following examples.

$10^7$ of human thymocytes were intraperitoneally administered and immunized into Balb/c mice at two weeks interval for six weeks. The spleen of Balb/c mice was removed 3 days after last administration to prepare the spleen cell suspension. monoclonal antibodies were produced by fusing the spleen cells of Balb/c mice immunized with human thymocytes with SP2/0-Ag14 mouse myeloma cells resistant to 9-azaguanine. Cell fusion method followed Koeler and Milstein method (Koeler and Milstein, 1975, Nature, 256, 495–497). $10^8$ spleen cells were fused with $10^7$ myeloma cells using 50% polyethylene glycol 4000. The cells were washed and resuspended in DEAE media containing 20% bovine serum albumin, 100 $\mu$m hypoxanthine, 0.44 $\mu$m aminopterin and 16 $\mu$M thymidine (HAT media). The cells were inoculated to four 96-well plates and cultured at 37° C. 5% $CO_2$ in incubator. When colonies were formed after two weeks, the supernatant was prepared and the reactivity of antibody was observed using enzyme-linked immunosorbent assay (ELISk) and flow cytometry.

The well containing more than $10^5$ cells per well was regarded as positive group. Cells were taken from the well containing highly reactive antibody, and subcloned 0.5 cell per well by limiting dilution assay to produce stable hybridoma clone with high reactivity of antibody. This hybridoma clone secretes antibody into the media and the supernatant was stored for the next steps.

EXAMPLE 2

In order to discover a clone which secretes antibody recognizing the specific cell surface antigen on cortical thymocytes among the hybridoma clones produced by Example 1, the immunoperoxidase staining was carried out on the slide of 4 $\mu$m thick of fresh tissue and paraffin embedded tissue using the supernatant of the hybridoma clone produced by Example 1 according to avidin-biotin complex (ABC) staining method by binding avidin with biotin. The supernatant of monoclonal cell was used as primary antibody. The paraffin embedded tissue was treated with normal mouse serum and allowed to stand for 1 hour to prevent nonspecific background staining after removal of paraffin. After adding a primary antibody, they were allowed to stand overnight and washed three times with PBS. Biotinylated goat-anti-mouse immunoglobulin used as a secondary antibody was added. It was allowed to stand at room temperature for 1 hour, washed three times with phosphate buffered saline(PBS). Then streptavidin and horse-radish peroxidase conjugate was added. AEC kit manufactured by Burlingame was used to stain the cell. $H_2O_2$-aminoethyl carbazole solution was added, treated for 20 minutes and washed three times with PBS. It was observed under light microscopy after covering with cover glass of 80% glycerol gelatin.

Figure 1:
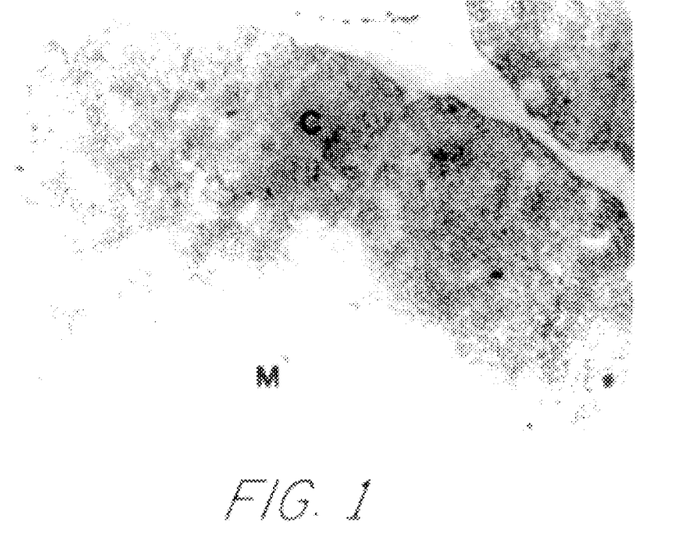
FIG. 1 is the photograph of immunohistochemical staining of thymus by supernatant of hybridoma clone producing anti JL-1 antibody.

Hybridoma clone lines producing antibody specific for human cortical thymocytes were selected. One of clones whose antibody recognized only cortical thymocytes was named as H-JL1. The antigen recognized by anti-JL1 antibody was named as JL1 and the monoclonal antibody as anti-JL1 antibody. FIG. 1 is a photograph of immunohistochemical analysis staining thymus with the supernatant of hybridoma clone producing anti JL-1 antibody. As shown in FIG. 1, only cortical thymus is positive and most of cortical thymocytes are positively stained. Cell surface of cortical thymocytes were strongly stained so the antigen recognized by anti-JL1 antibody is cell surface antigen. Medullary thymocytes were not stained with anti-JL-1 antibody. It proves that the JL1 is an antigen specific for the cortical thymocytes.

EXAMPLE 3

In order to obtain high concentration of antibody secreted by anti JL-1 antibody secreting hybridoma clone, ascites were prepared. Three weeks after 0.5 ml of pristane was administered intraperitoneally into Balb/c mouse, $10^7$ of H-JL-1 hybridoma clone cultured in DMEM containing 10% bovine serum were administered. After 2 to 3 weeks, ascites were collected. Then the concentration of antibody is 5 to 10 mg/ml. Only immunoglobulins responding to human thymocytes were purified because there are many contaminating proteins such as albumin in ascites. To purify antibody from ascites containing high amount of antibodies obtained from Balb/c mouse into which anti HJL-1 monoclonal hybridoma cells were intraperitoneally administered, Q-Sepharose chromatography and hydroxyapatite (Bio-gel HTP Gel manufactured by Pharmacia) chromatography were performed.

3.14 g of ammonium sulfate per 10 ml of ascites edema was slowly added on ice (precipitated with 50% of $(NH_4)_2SO_4$). The mixture was centrifuged at 15,000 rpm for 30 min, resuspended in deionized water and dialyzed in 1 liter of buffer solution (20 mM phosphate, pH 7.4). The solution was passed and absorbed in Q-Sepharose column previously equilibriated with buffer solution (20 mM phosphate, pH 7.4), and then the buffer solution was again passed through the column to remove free proteins in the column. After which the protein acsorbed in column was eluted with linear gradient 0M to 0.8M of NaCl using buffer solution I (20 mM phosphate, pH 7.4) and buffer solution II (20 mM phosphate and 0.5M NaCl, pH 7.4). Each fraction was electrophoresed in SDS-PAGE and the fractions containing anti JL-1 antibody were collected.

The fractions were then, dialyzed, and put into through hydroxyapatite column previously equilibrated with buffer solution (20 mM phosphate, pH 6.8). The fraction (20 mm phosphate, pH 6.8) was passed through the column to remove free proteins and was eluted with a linear gradient 0 to 0.3M of phosphate using buffer solution III (20 mM phosphate, pH 6.8) and buffer solution IV (300 mM phosphate, pH 6.8). Each fraction was electrophoresized in SDS-PAGE and the fractions containing more than 95% of anti JL-1 antibody were collected. Anti JL-1 antibody collected was dialyzed in appropriate buffer solution and stored. 5 to 10 mg of anti JL-1 antibody was prepared from 1 mg of ascites by repeated experiments.

Figure 2:
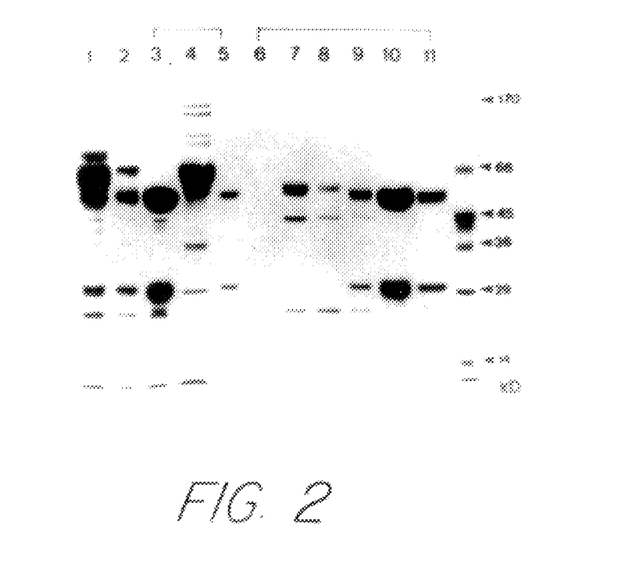
FIG. 2 is the photograph of 10% SDS-PAGE analysis of the resulting product and the intermediate material at each step according to the purification step of anti JL-1 antibody.

The electrophoresis of the intermediate product and the final product in 10% SDS-PAGE was shown in FIG. 2. The first lane is ascites, the second lane is the 50% ammonium sulfate precipitates before Q-Sepharose chromatography and the third and the fourth lanes are some of the fractions eluted from the proteins absorbed to Q-Sepharose column, the fifth lane is the fractions collected from the fractions containing many anti JL-1 antibody among the fractions of Q-Sepharose chromatography before hydroxyapatite column chromatography, and the sixth, the seventh, the eighth, the ninth, the tenth and the eleventh are some of the fractions eluted from the proteins adsorbed by hydroxyapatite column.

EXAMPLE 4

The present example was carried out according to immunochemical assay of Example 2 to confirm whether JL-1 antigen is expressed in normal tissue except thymus using anti JL-1 antibody purified from Example 3 as primary antibody. Table I below is the distribution of JL-1 antigen in each of the various tissues. Except for thymocytes, all other tissue including peripheral lymphoid tissue, cerebellum, pancreas tissue, ovary and testis, skin, lung, adrenal, and kidney were not positive with staining. This finding confirms that JL-1 is an antigen specific to cortical thymus.

TABLE I

| Histologic classification | No. of cases | No. of JL-1 Positive | Note |
|---|---|---|---|
| Lymphoid System | | | |
| lymph node | 5 | –* | |
| tonsils | 3 | – | |
| thymus | 6 | +++ | cortex staining |
| spleen | 2 | – | |
| Nervous System | | | |
| cerebrum | 3 | – | |
| cerebellum | 4 | – | |
| Gastrointestinal System | | | |
| esophagus | 3 | – | |
| stomach | 3 | – | |
| small intestine | 1 | – | |
| large intestine | 2 | – | |
| liver | 3 | – | |
| pancreas | 2 | – | |
| vermiform appendix | 2 | – | |
| Reproductive System | | | |
| testicles | 2 | – | |
| ovary | 2 | – | |
| uterus | 3 | – | |
| The Others | | | |
| skin | 3 | – | |
| lungs | 3 | – | |
| adrenal gland | 3 | – | |
| kidney | 2 | | |

*a negative reaction

EXAMPLE 5

Example 2 and Example 4 show that JL-1 antigen was expressed only on cortical thymocytes. In this example JL-1 antigen on normal cell and malignant hematopoietic cells were investigated by flowcytometric analysis. $1\times10^6$ cells were added into Falcon tube, centrifuged at 1,500 rpm for 5 min, and cell pellet of $1\times10^6$ cells per 100 μl was suspended in PBS. 100 μl of the suspension was distributed in test tubes and 100 μl of anti JL-1 antibody solution containing 1 μg of purified anti JL-1 antibody was added and stirred. The solution was reacted at 4° C. for 30 min, centrifuged at 1,500 rpm for 5 min, and the pellet was washed twice with PBS to remove the unreacted antibody. The pellet was suspended in 50 μl of the solution containing diluted secondary antibody (FITC-conjugated goat anti-mouse Ig manufactured by Zymed) and reacted at 4° C. for 30 min in a darkroom. 150 μl of PBS was added, centrifuged and cells were washed twice with PBS. Finally 200 μl of PBS was added to the cell pellet after centrifugation. The ratio of positive cells and the intensity of staining were analyzed by flowcytometry (FACSscan manufactured and sold by Bectom-Dickinson). Antibodies directly combined with FITC (Fluorescence Isothiocyanate) or PE (Phycoerythrin) were used as anti JL-1 antibody. In this case it was not necessary to use the secondary antibody for fluorescence. The result is given in Table II.

Table II below shows the expression of JL-1 antigen on the cell surface of normal cell, normal spleen cell, bone marrow cell, PBMC (Peripheral Blood Mononuclear Cell), activated PBMC cultured in the medium containing 10 μg/ml of PHA (Phytohemagglutinine), 3 μg/ml of PWM (Pokeweed mitogen), and 0.5 μg/ml of anti CD3 antibody. All of them were negative to JL-1 antibody. The positive response appeared only on thymocytes and 80–90% of cells before and after birth expressed JL-1 antigen. That is, JL-1 antigen was proved to be an antigen specific for thymocyte as previously shown in Example 4.

TABLE II

| Histologic classification | No. of cases | No. of JL-1 Positive |
| --- | --- | --- |
| Thymocytes fetal | | |
| 16 to 21 wks | 4 | 82.4 + 8.9 |
| 22 to 27 wks | 5 | 90.4 + 4.5 |
| 28 to 33 wks | 2 | 96.2 + 3.0 |
| postnatal | 6 | 91.3 + 6.0 |
| Spleen cell | 4 | – |
| Bone marrow cell | 6 | – |
| PBMC | 54 | – |
| Activated PBMC | | |
| PHA (10 μg/ml) | 5 | – |
| PWM (3 μg/ml) | 5 | – |
| anti-CD3 (0.5 μg/ml) | 5 | – |

–: negative response

EXAMPLE 6

Figure 3:
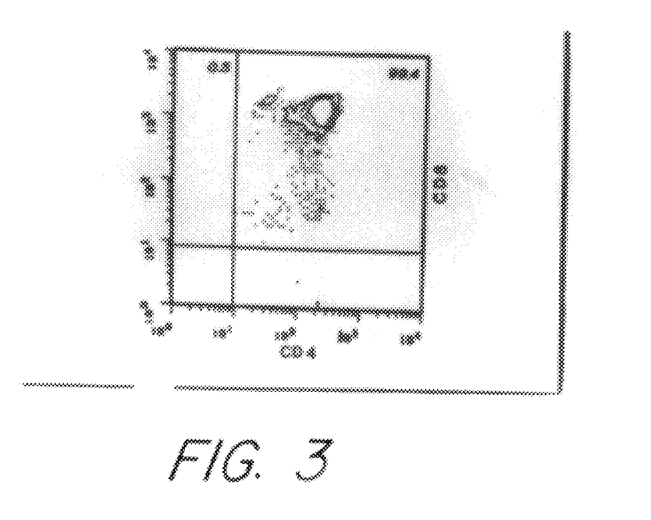
FIG. 3 is the photograph of the expression of CD4 and CD8 molecules on the cell surface of JL-1 positive thymocytes using two color FACS.

In order to determine when JL-1 antigen is expressed during thymic ontogeny, JL-1 positive cells were purified using anti JL-1 antibody, and two color FACS analysis was carried out using anti-CD4 antibody and anti-CD8 antibody. The method of analysis followed the method described above, FITC conjugated anti-CD4 antibody was used as anti-CD4 antibody and PE conjugated anti-CD8 antibody as anti-CD8 antibody. FIG. 3 is the result of two color FACS analysis showing the expression of CD4 and CD8 on JL-1 positive thymocyte purified by panning procedure. More than 99% of JL-1 positive cells were proven to be CD4 and CD8 double positive cells. That is, JL-1 positive cells were common thymocytes.

Marker analysis using anti JL-1 antibody shows a cell surface expression of JL-1 antigen on leukemia cells by flowcytometer. B lymphocyte, monocyte and tumor cell originated from myelocyte were negative to JL-1 antigen. T lymphocyte originated from common thymocyte was positive to JL-1 antigen and other T lymphocyte tumor cells were negative. However, as seen in table III, leukemic cells of 50–60% of various types of leukemic patient were positive for JL-1 antigen (Table 3). Therefore, JL-1 antigen and anti-JL-1 antibody could be a powerful diagnostic and therapeutic tools for various types of leukemia and T lymphoblastic lymphoma.

TABLE III

| | | Number of cases | |
| --- | --- | --- | --- |
| Type of leukemia | Number of cases | JL1 -positive | JL1 -negative |
| T-ALL | 11 | 10 (83.1 ± 16.6)* | 1 (2.0) |
| B-ALL, CALLA(+) | 18 | 15 (72.7 ± 19.3) | 3 (0.67 ± 0.94) |
| B-ALL, CALLA(-) | 1 | 1 (74) | 0 |
| AML | 24 | 19 (61.5 ± 29.7) | 5 (4.2 ± 3.9) |
| Acute biphenotypic leukemia | 4 | 3 (63.3 ± 19.2) | 1 |
| Adult T cell leukemia | 1 | 1 (58.0) | 0 |
| Total | 59 | 49 | 10 |

*Average of positive cell percent ± standard deviation

EXAMPLE 7

The present example was carried out to show that the specific immunohistochemical staining of thymus in Example 4, and the specific fluorescence staining of tumor cells originated from thymocytes in Example 5 and hematopoietic system in Example 6 are the result of the specific binding by antigen recognition region ($V_H+V_L$) of anti JL-1 antibody, not that of the binding by Fc receptor on tumor cell surface originated from cortical thymocytes. To accomplish the purpose of the example, Fc region of antibody was removed by protease, F(ab')$_2$ fragment and Fab fragment were purified, and immunohistochemical staining of thymus and flowcytometry of thymocytes were carried out. Generally, when the antibody of Balb/c mouse is IgG1 type and treated with papain, about 50 KDa of Fab fragment and Fc fragment were produced and when treated with pepsin, about 102 KDa of F(ab')$_2$ was produced and Fc fragment was digested into small fragments.

To prepare F(ab')$_2$ of anti JL-1 antibody, 10 mg of anti JL-1 antibody was dissolved in deionized water and dialyzed in 1 liter of buffer solution (0.1M citrate, pH 3.5). To the solution, 0.1 to 0.2 mg of pepsin manufactured and sold by Sigma was added, reacted at 37° C., and observed the degree of digestion, and upon occurring sufficient reaction the solution was neutralized by adding 1/10 volume buffer solution to complete the digestion of protein by pepsin. The solution was dialyzed in buffer solution (20 mM phosphate, pH 8), applied onto Q-sepharose column previously equilibrated with buffer solution (20 mM phosphate, pH 8.0) and then buffer solution (20 mM phosphate, pH 8.0) was passed through the column to remove free proteins, and then eluted with a gradient of 0 M to 0.5M of NaCl using buffer solution I (20 mM phosphate, pH 8.0) and buffer solution II (20 mM phosphate and 0.5M NaCl, pH 8.0). Each fraction was electrophoresized in SDS-PAGE to collect the fractions containing F(ab')$_2$ fragment. The collected F(ab')$_2$ fragment was dialyzed in appropriate buffer solution and stored.

Figure 4:
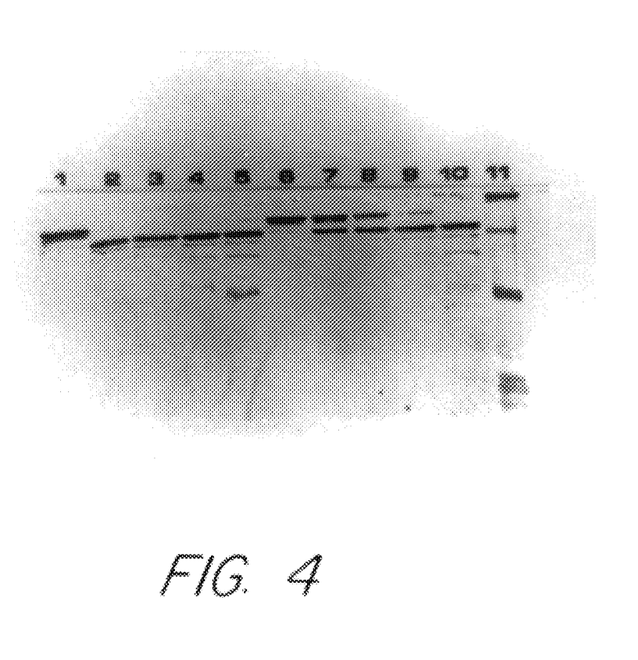
FIG. 4 is a photograph of 15% SDS-PAGE analysis of anti JL-1 antibody digested by pepsin at pH 3.5 and pH 3.8 for various time.

FIG. 4 is the result of electrophoresis of anti JL-1 antibody digested with pepsin at 37° C. in pH 3.5 and pH 3.8 buffer solutions (0.1M citrate) for various period. The first to fifth lanes are at pH 3.5 for 0, 0.5, 1, 2, and 4 hours, the sixth to tenth lanes are at pH 3.8 for 0, 0.5, 1, 2, and 4 hours, and the eleventh lane is standard proteins with known molecular weights. The upper thick bands of the first and the sixth lanes are anti JL-1 antibody, and the thick band below the anti JL-1 antibody band of the second to the fifth lanes and the seventh to the tenth lanes were F(ab')$_2$ fragment having 102 KDa molecular weight.

To prepare Fab of anti JL-1 antibody, 10 mg of anti JL-1 antibody was dissolved in 5 ml of buffer solution (20 mm phosphate, pH 7 to 8) and dialyzed in 1 liter of buffer solution (20 mM phosphate, pH 7 to 8). To the solution, cystein and EDTA were added to be 15 mM and 1 mM resulting solutions, 0.2 mg of papain manufactured and sold by Boehringer Mannheim was added, reacted at 37° C., and observed the degree of digestion. Upon occurring sufficient reaction the solution was neutralized by adding 1/10 volume 1M iodoacetamide solution to complete the digestion of protein by papain. Fab fragment was purified according to the process for preparing F(ab')$_2$. The fragment thus collected was dialyzed in appropriate buffer solution and stored.

Figure 5:
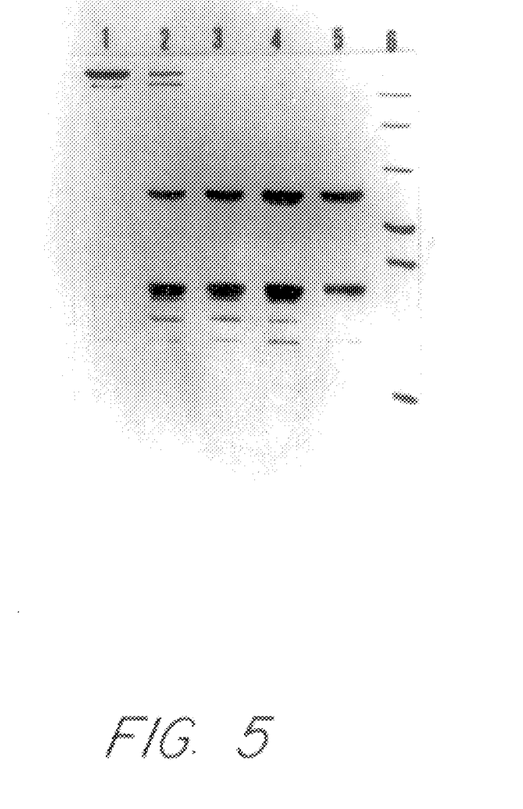
FIG. 5 is a photograph of 15% SDS-PAGE analysis of anti JL-1 antibody digested by papain.

FIG. 5 is the result of electrophoresis of anti JL-1 antibody digested with papain at 37° C. in buffer solution (20 mM phosphate, pH 7.0) for various period. The first to fifth lanes are for 0, 0.5, 1, 2, and 6 hours, the sixth lane is standard proteins with molecular weights of 116, 85, 53, 39, 27, and 14 Kda respectively from the top. The upper thick band of the first lane was anti JL-1 antibody, and the thick band between 53 KDa and 39 KDa of standard proteins was Fab fragment having 50 KDa molecular weight.

F(ab')$_2$ fragment and Fab fragment thus purified was immunohistochemically stained on thymus according to Example 4 and the positive response was showed. The JL-1 antigen of tumor cells originated from thymocytes and cortex thymocytes were observed by flowcytometer according to the processes of Example 5 and Example 6 and it showed the positive response as Example 5 and Example 6. It means that the recognition by the anti JL-1 antibody of cell expressing the JL-1 on the cell surface is because of the specific recognition by antigen recognition region of anti-JL-1 antibody, not because of the nonspecific binding of anti-JL-1 antibody by Fc receptor on tumor cell surface originated from cortex thymocytes via Fc region. Anti-JL-1 antibody fragment having antigen recognition region is useful in the recognition of JL-1 antigen as anti-JL-1 antibody.

EXAMPLE 8

In order to investigate the possibility to use the antibody against JL-1 protein for the treatment of leukemias and lymphomas, the following in vitro test was carried out. Anti JL-1 antibody in RPMI media containing 30% pooled human serum of AB blood type without complement inactivation were added to 5×10$^5$ T lymphoblastic leukemia cells/ml, cultured for 12 hours, and observed the viability of tumor cells using Trypan blue staining. This finding strongly suggest that tumor cells can be killed when antibody against JL-1 protein was administered to the leukemic cells. Tumor cell killing by anti JL-1 antibody is mediated by cell lysis which is dependent on either complement system and Fc portion of the antibody. This procedure is considered to be the result of complement meditated lysis.

EXAMPLE 9

Figure 6:
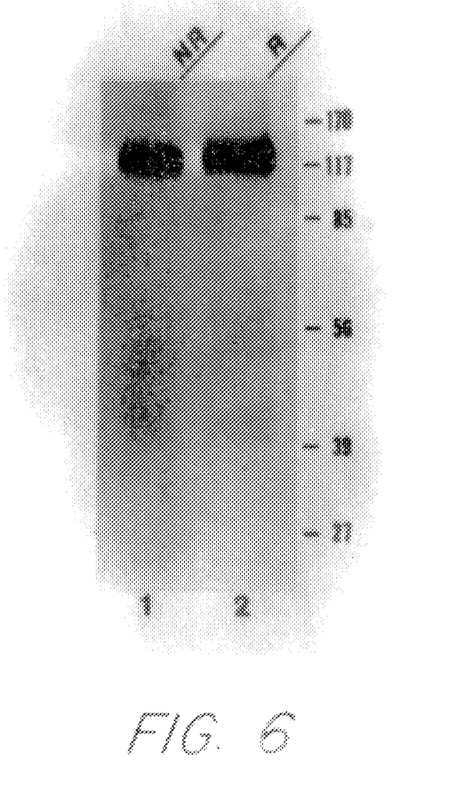
FIG. 6 is a photograph of SDS-PAGE analysis of JL-1 protein which is immunoprecipitated with anti JL-1 antibody conjugated bead after radioisotope labelling of thymocytes.

In order to observe biochemical characteristics of JL-1 protein, immunoprecipitation and SDS-PAGE were carried out. 1×10$^7$ of human thymocytes or Molt-4 tumor cells washed with PBS (phosphate buffer solution) was suspended in 100 ml of PBS. 5 µg of lactoperoxidase and 250 µCi of Na$^{125}$I was added, H$_2$O$_2$ added and reacted for 3 min, and washed with PBS. Cells with the cell surface labelled with $^{125}$I were suspended in lysis buffer solution (50 mM Tris-HCl, pH 7.4, 150 mM NaCl, 0.5% w/v Nonidet P-40 and 1 mM PMSF) to be 1×10$^7$ cells per 1 ml, and shaken at 4° C. for 30 minutes. The lysate was centrifuged at 3,000 rpm for 7 min, the supernatant was taken, and the pellet was discarded. The supernatant of lysate was reacted with 20 µl of protein A-Sepharose CL-4B bead manufactured by BioRad for 2 hours, and then reacted with protein A-Sepharose bead conjugated with rabbit anti-mouse Ig to preclear nonspecific materials. The remaining lysate was reacted with 20 µl of rabbit anti-mouse Ig-protein A-Sepharose bead conjugated with anti Jl-1 antibody for more than 12 hours. The precipitate was boiled in buffer solution for electrophoresis (0.125M Tris HCl, pH 6.8, 4% SDS, 20% glycerol and 1% β-mercaptoethanol) for 10 min to elute the antigen and electrophoresed in SDS-PAGE to find a desired protein band. An 8% acrylamide gel was used for electrophoresis, and after the gel was dried and it was exposed to Hyper film-MP manufactured by Amersham at −70° C. for 1 day for autoradiography FIG. 6 shows a SDS-PAGE analysis of JL-1 protein which was immunoprecipitated after thymocytes were labelled with radioisotope. The first lane was an electrophoresis under nonreducing conditions of JL-1 protein prepared by immunoprecipitation of the lysate of thymocytes and the second lane was an electrophoresis under reducing conditions. A band with molecular weight of 120,000 Dalton was seen on both reducing and nonreducing conditions. This means that JL-1 protein comprises a single polypeptide chain. Also, the band under reducing condition was appeared to migrate slowly suggesting that there is a disulfide bond in the protein. An electrophoresis analysis after the treatment of JL-1 protein with endoglycosidase-F results in faster migration of the protein suggesting that JL-1 is a glycoprotein. Therefore, JL-1 protein is a glycaprotein having a single polypeptide with 120,000 Dalton of molecular weight. CD1a, CD1b, and CD1c have been known as proteins which are expressed only on cortical thymocytes during the development of T cells. CD1a is, however, a heterodimer consisting of a polypeptide with 49,000 Dalton molecular weight and a polypeptide, called β2m, with 12,000 Dalton molecular weight. CD1b is a protein consisting of polypeptides with 45,000 Dalton molecular weight and β2m, and CD1c is a protein consisting of polypeptides with 43,000 Dalton molecular weight and β2m. However, these proteins are different from the protein of the present invention. Further, CD1a is appeared on cell surfaces of skin dermal dendritic cells, Langerhans cells and brain astrocytes, and CD1b is on cell surface of skin dermal dendritic cells, brain astrocytes and B lymphocytes, and CD1c is on skin dermal dendritic cells and B lymphocytes. Purification of JL-1 molecule were done using affinity column which was made by conjugation of purified 100 µg of anti-JL-1 antibody to sepharose beads. Approximately 20 µg of antigen were collected by boiling of bead with PAGE sample buffer. This protein were diagested with trypsin and a representative fraction were selected using HPLC. Sequencing was done using the Edman degradation method, the sequences are as follows. V(Valine)-L(Leucine)-P(Proline)-S(Serine)-V (valine)-F(Phenylalanine)-C(Cysteine)-A(Alanine)-I (Isoleucine)-T(Threonine) (SEQ ID No: 1). Therefore JL-1 protein and anti JL-1 antibody is very useful for the diagnosis and treatment of leukemia and T-lymphoblastic lymphoma cells.

The JL-1 protein of the present invention is useful for the diagnosis of T cell lymphoblastic lymphoma and leukemia by determining whether JL-1 protein is expressed upon tissue examination or peripheral blood examination because thymocyte specific protein JL-1 is not found in normal tissues or activated peripheral blood except thymocytes. The paraffin embedded tissue is used for the tumor diagnosis. However, immature T cell antibody reactive with for such paraffin embedded tissue has not been found until now. JL-1 is stable in paraffin embedded tissue so that it is useful for the diagnosis of tumor. The antibody or ligand of the present invention is useful for the treatment T cell lymphoblastic lymphoma and leukemia expressing JL-1 antigen. The present antigen can be used as target material for the gene therapy because it is not expressed on normal tissues.

The above description of exemplary embodiments of biologically active polypeptides is illustrative of the present invention. Because of the variation which will be apparent to those skilled in the art, however, the present invention is not intended to be limited to the particular embodiments described above. The scope of the invention is defined in the following claims.

What is claimed:

1. An antibody that binds a cell surface protein expressed on human cortical thymocytes, wherein said cell surface protein is JL-1 and has a partial sequence of V(Valine)-L(Leucine)-P(Proline)-S(Serine)-V(Saline)-F(Phenylalanine)-C(Cysteine)-A(Alanine)-I(Isoleucine)-T(Threonine) (SEQ ID NO:1).

2. The antibody of claim 1, wherein said antibody is a monoclonal antibody.

3. The antibody of claim 2, wherein said monoclonal antibody is human or animal monoclonal antibody.

4. The antibody of claim 1, wherein said antibody is a polyclonal antibody.

5. The antibody of claim 4, wherein said polyclonal antibody is human or animal polyclonal antibody.

6. A cell producing the antibody of claim 1.

7. An antibody fragment that binds a cell surface protein expressed on human cortical thymocytes, wherein said cell surface protein is JL-1 and has a partial sequence of V(Valine)-L(Leucine)-P(Proline)-S(Serine)-V(Saline)-F(Phenylalanine)-C(Cysteine)-A(Alanine)-I(Isoleucine)-T(Threonine) (SEQ ID NO:1).

8. A cell producing the antibody fragment of claim 7.

9. An antibody of claim 1 comprising variable region of heavy chain ($V_H$) and variable region of light chain ($V_L$).

10. A composition comprising the antibody fragment of claim 9 linked to a toxic protein.

11. An antibody or fragment thereof having a label, wherein said antibody or fragment thereof binds a cell surface protein expressed on human cortical thymocytes, wherein said cell surface protein is JL-1 and has a partial sequence of V(Valine)-L(Leucine)-P(Proline)-S(Serine)-V(Saline)-F(Phenylalanine)-C(Cysteine)-A(Alanine)-I(Isoleucine)-T(Threonine) (SEQ ID NO:1).

12. An antibody produced by the cell line H-JL1 that has the deposit accession number KCLRF-BP-00010.

13. An antibody produced by the cell line H-JL1 that has the deposit accession number KCLRF-BP-00010, wherein said antibody binds a cell surface protein expressed on human cortical thymocytes, and wherein said cell surface protein is JL-1.

14. An antibody fragment according to claim 9 wherein said variable region of heavy chain ($V_H$) and said variable region of light chain ($V_L$) are combined using a linker polypeptide.

15. The composition of claim 10, wherein said antibody fragment and said toxic protein are combined to produce a fused protein.

16. A cell producing the antibody fragment of claim 9.

17. An antibody or fragment of claim 11, wherein said label is selected from the group consisting of radioisotope, fluorescent material, and staining material.

18. A method of producing the antibody of claim 1 comprising:
    a) immunizing an animal with human thymocytes;
    b) obtaining cells that produce antibodies specific for a cell surface protein expressed on human cortical thymocytes wherein said cell surface protein is said JL-1;
    c) fusing the cells obtained in (b) with a myeloma cell line to create hybridomas secreting said antibodies; and
    d) screening said hybridomas and selecting a hybridoma that produces an antibody that specifically binds to said JL-1.

19. A method of producing the antibody fragment of claim 7 comprising:
    a) immunizing an animal with human thymocytes;
    b) obtaining cells that produce antibodies specific for a cell surface protein expressed on human cortical thymocytes wherein said cell surface protein is said JL-1;

c) fusing the cells obtained in (b) with a myeloma cell line to create hybridomas secreting said antibodies; and d) screening said hybridomas and selecting a hybridoma that produces an antibody that specifically binds to said JL-1;

e) recovering said antibody; and g) preparing an antibody fragment from said antibody.

20. A method of producing the antibody of claim 9 comprising a) immunizing an animal with human thymocytes;

b) obtaining cells that produce antibodies specific for a cell surface protein expressed on human cortical thymocytes wherein said cell surface protein is said JL-1;

c) fusing the cells obtained in (b) with a myeloma cell line to create hybridomas secreting said antibodies; and d) screening said hybridomas and selecting a hybridoma that produces an antibody that specifically binds to said JL-1.

* * * * *